United States Patent [19]

Kaufman

[11] 4,328,239

[45] * May 4, 1982

[54] 8-AMINOALKYLPSORALENS

[75] Inventor: Kurt D. Kaufman, Kalamazoo, Mich.

[73] Assignee: Elder Pharmaceuticals, Inc., Hamilton, Ind.

[ * ] Notice: The portion of the term of this patent subsequent to May 26, 1998, has been disclaimed.

[21] Appl. No.: 236,765

[22] Filed: Feb. 23, 1981

Related U.S. Application Data

[63] Continuation-in-part of Ser. No. 73,907, Sep. 10, 1979, Pat. No. 4,269,851.

[51] Int. Cl.$^3$ ................. C07D 493/04; A61K 31/365
[52] U.S. Cl. ..................................... 424/279; 424/59; 548/463; 549/282
[58] Field of Search .................. 260/343.21; 424/279, 424/59

[56] References Cited

U.S. PATENT DOCUMENTS

| | | | |
|---|---|---|---|
| 4,124,598 | 11/1978 | Hearst et al. | 260/343.21 |
| 4,169,204 | 9/1979 | Hearst et al. | 260/343.21 |
| 4,269,851 | 5/1981 | Kaufman | 260/343.21 |

OTHER PUBLICATIONS

Hearst et al. (II), Chem. Abst. 87:78962f, 1977.
Issacs et al., Chem. Abst. 86:135108n.
Johnston et al., Chem. Abst. 87:147284a.
Shen et al., Chem. Abst. 88:59494j.

*Primary Examiner*—Jane T. Fan
*Attorney, Agent, or Firm*—Gordon W. Hueschen

[57] ABSTRACT

The invention relates to 8-aminoalkylpsoralens, having essentially no erythematic photosensitizing activity but at the same time having substantial DNA-binding photosensitizing activity, making them of especial interest from the standpoint of suntanning and psoriasis treatment, characteristics which are unpredictable when the compounds are compared with psoralens of similar but different structure.

6 Claims, No Drawings

8-AMINOALKYLPSORALENS

This application is a continuation-in-part of my prior-filed copending application Ser. No. 073,907, filed Sept. 10, 1979, now U.S. Pat. No. 4,269,851, issued May 26, 1981.

BACKGROUND OF INVENTION

1. Field of Invention

Chemical compounds, photochemotherapy, compounds having an enhanced combination of photosensitizing properties for use in photochemotherapy, selective photosensitizing agents.

2. Prior Art

Psoralens have been used for years as dermal photosensitizing agents, e.g., in the treatment of vitiligo. Their topical and/or oral application, followed by irradiation with light, results in stimulation of melanin, thus producing a tanning effect. They have accordingly also been used for such cosmetic purpose. More recently, psoralens have been found useful in the photochemotherapeutic treatment of psoriasis, in which case they are administered orally or topically to the subject, whose skin is subsequently exposed to controlled ultraviolet radiation, as in Psoralite (TM) apparatus. A high percentage of remissions of this disease have been effected in such manner.

The effectiveness of a psoralen for such uses and for such purpose has in the past been related to its ability to produce erythema upon the skin upon irradiation. Psoralens also have other uses, and their uses, as well as underlying rationale and theory, are partially elucidated in U.S. Pat. Nos. 4,124,598 and 4,130,568, and are otherwise well-known in the art from various preexisting publications.

Rather recently, it has been found that the erythema, produced upon the skin of a patient or animal upon irradiation with ultraviolet light "A" in a so-called PUVA evaluation or application, after administration of psoralen to the subject, is associated with the linear structure of psoralens. This makes it possible for psoralens to engage in photocycloaddition reactions with double bonds of pyrimidine bases of macromolecules, such as present in the complementary strands of DNA (deoxyribonucleic acid), in a manner such that two double bonds of the psoralen compound react so as to produce two (2) cycloadditions with two (2) separate molecules of the pyrimidine base, as present in the complementary strands of DNA, thereby forming an interstrand crosslinkage. Such interstrand crosslinkages occur in photoreactions between highly erythematic linear psoralens and DNA. On the other hand, some psoralens, because of their angular structure, can engage, for geometric reasons, only one of the two photoreactive sites, thus effecting a single cycloaddition to only one of the two complementary strands of DNA with consequent production of a monofunctional adduct. In other words, psoralen compounds in the photoreaction with DNA can form either or both of monofunctional and bifunctional adducts, and this capacity varies with the type of psoralen compound involved, some compounds forming essentially only monofunctional adducts, whereas other compounds form solely or a preponderance of bifunctional adducts or interstrand crosslinkages. The ability or capacity to form only monofunctional and not bifunctional adducts, or at least minimization of bifunctional cycloaddition or bifunctional adduct formation, is now considered desirable from the standpoint that the consequences deriving from bifunctional damage are considered to be more serious from a biological repair standpoint than the consequences deriving from monofunctional cycloaddition or adduct effects. This means that it is at least no longer considered necessary that a compound exhibit strong bifunctional effects, as evidenced by a high degree of erythema in usual test procedures, for it to be useful in photochemotherapy, but that it is even preferred for it to produce monofunctional adducts or a single cycloaddition without interstrand crosslinkage to DNA. Psoralen compounds which produce monofunctional adducts only, or at least in preponderance, have been found effective in the treatment of psoriasis and in producing other desirable effects, such as tanning, even though they do not cause interstrand crosslinkages and consequent erythema. Such unique properties therefore constitute desirable and much sought after criteria or desideratum in the evaluation of photosensitizing compounds but, as already stated, up until the present time such psoralen compounds as produce monofunctional DNA adducts have been angular in their nature, such as some isopsoralens (or angelicins). However, the compounds of the present invention, despite their linear structure, for unknown reasons, are characterized by inability to crosslink DNA molecules and cause erythema, while nevertheless possessing ability to cause DNA monoaddition and production of monofunctional adducts, a totally unpredictable combination of characteristics for linear psoralen compounds. Further, linear psoralens are also characterized by established and recognized reactivity with ribonucleic acids (RNA), and accordingly the new psoralen compounds find use in the study of secondary structures of nucleic acids, as inhibitors of RNA replication, and in the inactivation of viruses, as well as in the photochemotherapy of psoriasis and in suntanning, all important uses.

The standard tests and test procedures, and their significance, are fully elucidated in the following publications:

F. Dall'Acqua, S. Marciani, G. Rodighiero: Interstrand crosslinkages occurring in the photoreaction between psoralen and DNA. FEBS letters 9, 121 (1970); F. Dall'Acqua, S. Marciani, L. Ciavatta, G. Rodighiero: Formation of interstrand cross-linkings in the photoreactions between furocoumarins and DNA. Zeitschrift Naturforsch. 26b, 561 (1971); Baccichetti et al., Z. Naturforsch. 34c, 811–814 (1979); Bordin et al., Biochimica et Biophysica Acta 447, 249–259 (1976); Baccichetti et al., Experientia 35, 183 (1979); and see U.S. Pat. Nos. 4,124,598 and 4,130,568, as well as Hearst et al., Nucleic Acids Res. 1977, 4(5), 1339–1347; Isaacs et al., Biochemistry 1977, 16(6), 1058–1064; Shen et al., J. Mol. Biol. 1977, 116(4), 661–679; and Johnson et al., Science 1977, 197(4306), 906–908.

The unique linear psoralen compounds of the present invention then, which possess the characteristic, when employed in PUVA therapy, of forming only monofunctional adducts or essentially so, without concurrent interstrand DNA crosslinkages or erythema, thus finding employment and use in the foregoing manners, particularly in the photochemotherapy of tanning and psoriasis, should be welcome additions to the physicians' armamentarium of useful drugs.

OBJECTS OF THE INVENTION

It is an object of the invention to provide novel psoralen compounds. It is a further object to provide novel psoralen compounds of unique structure which have a beneficial or enhanced combination of characteristics when compared with psoralen compounds of similar but different structure. It is an additional object to provide novel psoralen compounds having beneficial or enhanced photosensitizing characteristics in accord with the foregoing stated criteria. It is a still further object to provide novel psoralen compounds having beneficial or enhanced photosensitizing characteristics, relatively low toxicity, and of a structure differing essentially from known psoralen compounds, the beneficial combination of properties of which could not be predicted on a basis of known structure-activity relationships. Still other objects will be apparent to one skilled in the art and still additional objects will become apparent hereinafter from the following description and claims.

SUMMARY OF THE INVENTION

The present invention relates to 8-aminoalkylpsoralens having beneficial or enhanced photosensitizing activity, especially oral activity, as well as low toxicity, when compared with psoralens of similar but different structure. It is particularly concerned with 8-primaryaminoloweralkylpsoralens, and especially 8-aminomethylpsoralen and salts thereof. It is to be noted that the compounds of this invention have only the single eight (8) carbon atom aminoalkyl substituent and not the 8-methyl or 8-methoxy substituent as in the prior art compounds trisoralen (4,5', 8-trimethylpsoralen), 8-methoxpsoralen, or the compounds of U.S. Pat. Nos. 4,124,598 or 4,130,568. Despite this fact, and the fact that they are characterized by essential absence of DNA crosslinking and/or erythematic photosensitization activity, they are characterized by DNA-binding (monocycloaddition or monofunctional adduct production) which exceeds that of 8-methoxypsoralen, a widely-recognized and commonly-employed photosensitizing agent. These new compounds are therefore characterized by surprising and unpredictable selective photosensitization activity, i.e., DNA-binding activity without concurrent erythematic activity, according to the aforesaid criteria, as well as a relatively low toxicity.

The compounds of the invention have the formula:

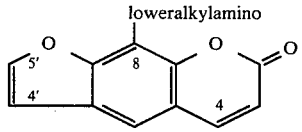

8-primaryaminoloweralkylpsoralen, wherein loweralkyl is preferably methyl.

DETAILED DESCRIPTION OF THE INVENTION

The following preparations and Examples are given by way of illustration only.

Starting 8-alkylpsoralens and their method of preparation are known. Caporale and Bareggi, Gazz. Chim. Ital. 98, 444–457 (1968); P. N. Confalone, Ger. Offen. No. 2,741,233. Their preparation is from known 7-allyloxy-8-alkylcoumarins via 6-allyl-7-hydroxy-8-alkylcoumarins, e.g., 6-allyl-8-methylumbelliferone, also known compounds having a known method of preparation. Rangaswami and Seshadri, Proc. Indian Acad. Sci. 7A, 8–12 (1938). According to the invention, variation in the alkyl group in the end product is effected by variation in the starting 8-alkylpsoralen, other reaction steps remaining the same. Alternatively, the end products of this invention may be prepared using the Delepine method (Delepine, Bull. Soc. Chim. France 13, 358 (1895); Mannich and Hahn, Berichte 44, 1542 (1911), which sometimes permits higher overall yields.

Thin layer chromatography (TLC) was performed on Silica Gel $GF_{254}$ glass-backed slides, 250 microns thick, by Analtech, Inc. The eluent was benzene:2-butanone::17:3 unless otherwise indicated. NMR spectra were run on Perkin-Elmer Model R-24B. Melting points were taken on a Fisher Digital Melting Point Analyzer, Model 355, or on a Thomas Hoover Capillary Melting Point Apparatus, and all are uncorrected.

8-AMINOMETHYLPSORALEN

Preparation 1: 8-Methylpsoralen

Osmium tetroxide (1.0 g) was dissolved in water (100 ml), purged with argon, and placed in a refrigerator. 6-allyl-7-hydroxy-8-methylcoumarin (4.0 g., 18.5 mmols) was dissolved in methanol (120 ml.) and water (3 ml.), and potassium periodate (10 g., 40 mmoles) was added. The $OsO_4$ solution (20 ml.) was added dropwise from a buret to the reaction mixture while it was stirring. After 4-½ hours of stirring at room temperature, the reaction mixture was diluted with methylene chloride (200 ml.) and the solid residue was collected by filtration and washed with two fifty ml portions of $CH_2Cl_2$. The combined $CH_2Cl_2$ solutions were then extracted with two 100-ml portions of saturated brine. The aqueous layers were combined and washed with methylene chloride ($CH_2Cl_2$) (200 ml). The $CH_2Cl_2$ layers were combined, dried ($MgSO_4$), and concentrated (Rotovap$^{TM}$) to give 3.652 g (90.5%) of yellow-white crystals of 4', 5'-dihydro-5'-hydroxy-8-methylpsoralen, mp. 156.5°–159° C. TLC (Benzene: 2-Butanone; 4:1) revealed one major spot and three minor spots.

This crude product (1.641 g, 7.5 mmol) was heated on a steam bath for fifteen minutes in thirty ml of 85% $H_3PO_4$. The mixture was poured into water (150 ml) and the resulting light brown precipitate filtered and washed with water to give 1.3 g (87%) of desired product, mp 120°–140° C. TLC (Benzene:2 Butanone; 4:1) revealed one major spot and two minor spots. Fisher A-540 Alumina (130 g) and chloroform were used to prepare a column for chromatography. The crude material (1.3 g) was introduced to the column dissolved in fifty ml of chloroform. Elution with chloroform gave eighteen 25-ml. fractions. Numbers 6 through 14 were found by TLC (Benzene:2-butanone; 4:1) to contain pure compound and were combined and concentrated (Rotovap$^{TM}$) to obtain 0.876 g (67%) of 8-methylpsoralen, mp 149.3°–151.9° C., uncorrected. TLC (Benzene:2-Butanone; 4:1) revealed a single spot.

Preparation 1A: 8-Methylpsoralen (Using less $OsO_4$)

Potassium periodate (10 g, 40 mmol) was added to a solution of 6-allyl-7-hydroxy-8-methylcoumarin (4 g, 15.5 mmol) in methanol (120 mL). A portion (4.0 mL) of an aqueous $OsO_4$ solution (1 g/100 mL) was diluted with water (16 mL) and added to the stirred reaction mixture. After stirring for 18-½ hours, the mixture was diluted with methylene chloride ($CH_2Cl_2$) (200 mL) and filtered. The residue was washed with two portions (50 mL) of $CH_2Cl_2$, which were combined with the filtrate and washed with two portions (100 mL) of saturated brine. The aqueous layers were backwashed with $CH_2Cl_2$ (200 mL) and all $CH_2Cl_2$ layers were dried ($Na_2SO_4$) and concentrated in vacuo to obtain crude 4',5'-dihydro-5'-hydroxy-8-methylpsoralen (3.80 g, 94%). TLC (Analtech silica gel $GF_{254}$, 250μ, glass-backed, slides; 20% 2-butanone in benzene) showed no starting material, one minor spot near the origin, and a major spot of the desired product. All of the material (3.80 g, 17.4 mmol) was heated on a steam bath for thirty minutes in 85% $H_3PO_4$ (60 mL), poured into water (300 mL), and filtered to obtain crude 8-methylpsoralen (2.830 g, 81%). TLC showed traces of unreacted hemiacetal as well as an impurity near the origin, in addition to the desired product. A solution of the crude product in chloroform ($CHCl_3$) (HPLC grade, 150 mL) was poured onto a column of alumina (Fisher A-540, 280 g, packed in $CHCl_3$) which was developed with $CHCl_3$. Eighteen fractions (50 mL) were collected and monitored by TLC. Fractions 7 through 15 were combined and concentrated in vacuo to obtain pure 8-methylpsoralen (1.700 g, 49%), mp 149.9°–151.3° C. (previous run: mp 149.3°–151.9° C.). TLC showed only a single spot.

Preparation 2: 8-Bromomethylpsoralen

N-bromosuccinimide (4.446 g., 25.0 mmole), carbon tetrachloride (500 ml), 8-methylpsoralen (5.000 g., 25.0 mmole), and benzoyl peroxide (0.606 g., 2.50 mmole) were placed, in that order, in a 1000-ml round-bottom flask. The mixture was heated to reflux with constant stirring, and was protected from atmospheric moisture by a Drierite^TM drying tube. After four hours, a negative test was obtained with moist KI-starch paper. The hot mixture was filtered through a filter paper cone and the solid was washed with a small volume of hot carbon tetrachloride. The filtrate was cooled in a refrigerator. The crystallized material was collected by filtration and taken up in chloroform ($CHCl_3$) and extracted with four portions (ca. 50 ml each) of water. The $H_2O$ layers were each washed with a single portion of chloroform (10 ml). All chloroform layers were combined, dried ($MgSO_4$), and evaporated in vacuo to obtain the desired product (4.493 g., 64%), m.p. 191°–195° C. Recrystallization from $CCl_4$ followed by sublimation in vacuo at 195° C. gave an analytical sample, m.p. 202.7°–203.5° C., nmr ($CDCl_3$): 4.98 (s, 2H, —C$\underline{H}_2$—Br); 6.37 (d, 1, J=10Hz, C-3 H); 6.82 (d, 1, J=2 Hz, C-4' H); 7.63 (s, 1, C-5 H); 7.72 (d, 1, J=2 Hz, C-5' H); 7.74 (d, 1, J=10 Hz, C-4 H). Mass spectrum, m/e (relative intensity): 280 (9.76); 278 (10.55); 200 (13.13); 199 (100.00); 171 (28.94).

Anal. Calcd. for $C_{12}H_7O_3Br$: C, 51.64; H, 2.53; Br, 28.63. Found: C, 51.79; H, 2.67; Br, 28.60.

Preparation 3: 8-Phthalimidomethylpsoralen

To N,N-dimethylformamide (165 ml) were added crude 8-bromomethylpsoralen (1.65 g., 5.91 mmole) and potassium phthalimide (1.314 g., 7.04 mmole). This mixture, protected from atmospheric moisture by a Drierite^TM drying tube, was heated to 100° C. with stirring in an oil bath. After stirring constantly for six hours, the mixture was poured into 330 ml of ice-water. A tan precipitate was collected by filtration and dried to obtain the product (1.740 g., 85%), m.p. 254°–256° C. Thin layer chromatography showed a single spot, $R_f$=0.4. Recrystallization from 95% ethanol gave an analytical sample of small, off-white needles, m.p. 257°–258° C., nmr ($CDCl_3$): 5.32 (s, 2H, —C$\underline{H}_2$—N); 6.28 (d, 1, J=9 Hz, C-3 H); 6.68 (D, 1, J=3 Hz, C-4' H); 7.4–7.8 (m, 7H).

Anal. Calcd. for $C_{20}H_{11}O_5N$: C, 69.57; H, 3.21; N, 4.06. Found: C, 69.33; H, 3.46; N, 4.00.

8-Aminomethylpsoralen

A mixture of 8-phthalimidomethylpsoralen (0.250 g, 0.724 mmol), 95% ethanol (31 mL), glacial acetic acid (0.66 mL, 11.6 mmol), and 85% hydrazine hydrate (0.33 mL, 5.79 mmol) was refluxed with stirring (magnetic) until all of the phthalimidopsoralen had dissolved and until a TLC monitor showed the absence of starting material (ca. 3-¾ hours). The solution was concentrated in vacuo to a viscous yellow liquid, which was acidified with 1 N aqueous HCl (27 mL) and filtered to remove a precipitate, which was washed with two portions (7 mL) of 1 N aqueous HCl. Solid $NaHCO_3$ was added to the combined filtrate and washed until their pH reached ca. 8 and that solution was extracted with five portions (25 mL) of $CHCl_3$. The $CHCl_3$ extracts were combined, dried ($Na_2SO_4$), and evaporated in vacuo to obtain 8-aminomethylpsoralen (0.1152 g, 74%). Sublimation (130° C., 0.500 mm) of a portion gave a pure sample (52.5% recovery, 39% yield, 27% overall yield from 8-bromomethylpsoralen), mp 147°–50° C. A further purified sample melts at 156.8°–157.7° C. Structure is confirmed by NMR (CD $Cl_3$).

ALTERNATIVE PROCEDURE

Hexaminium salt of 8-bromomethylpsoralen

A solution of 8-bromomethylpsoralen (1.20 g., 4.30 mmole) in chloroform (ca. 20 ml) and a solution of hexamine (0.663 g., 4.73 mmole) in chloroform (ca. 20 ml) were combined and heated under reflux with constant stirring while being protected by a Drierite^TM tube. After three hours the mixture was cooled to room temperature and a cream-colored precipitate collected by filtration, washed with three portions of chloroform (10 ml each) and dried to obtain the desired product (1.681 g., 93%), m.p. 218°–220° C., nmr (DMSO-$d_6$): 4.28 (s, 2H, —C$\underline{H}_2$—N); 4.43 (s, 6); 5.17 (s, 6) hexamine protons; 6.41 (d, 1, J=9 Hz, C-3 H); 7.10 (d, 1, J=3 Hz, C-4' H); 8.2 (poorly resolved m, 3, C-4 H, C-5 H, C-5' H).

8-N-methyleneiminomethylpsoralen

The hexaminium salt of 8-bromomethylpsoralen (0.348 g., 0.83 mmole) was suspended in absolute ethanol (20 ml). The chilled, stirred suspension was saturated with HCl gas which had been bubbled through $H_2SO_4$ in a gas-washing tower. The reaction vessel was stoppered and the pale yellow solution was stirred at room temperature for twenty hours. The solvent was then evaporated in vacuo. The residue was brought to pH 8 by slow, portionwise addition of 5% aqueous $NaHCO_3$. A white precipitate was extracted into three portions of $CHCl_3$ (10 ml each). The $CHCl_3$ layers were combined, dried ($Na_2SO_4$), and evaporated in vacuo to obtain the crude product, nmr ($CDCl_3$): 3.72 (s, 2H, N=C$\underline{H}_2$); 4.29 (s, 2, —C$\underline{H}_2$—N); 6.25 (d, 1, J=10 Hz, C-3 H); 6.71, (d, 1, J=3 Hz, C-4' H); 7.50 (s, 1, C-5 H); 7.65 (d, 1, J=3 Hz, C-5' H); 7.70 (d, 1, J=10 Hz, C-4 H).

8-AMINOMETHYLPSORALEN

Crude 8-N-methyleneiminomethylpsoralen (obtained as described above, ca. 0.75 g.) was dissolved in 1.0 N $H_2SO_4$ (50 ml). This solution was distilled, with dropwise addition of deionized water to the still pot to maintain a constant volume of ca. fifty ml. Small fractions of the distillate were tested at approximately 75 ml intervals by the Tollens' test. Initial tests were positive, but a negative test was obtained after a distillate volume of ca. 150 ml. The residue in the still pot was cooled and then brought to pH 8 with solid NaHCO₃. The resulting suspension was extracted with chloroform (5×10 ml, 3×25 ml). All the chloroform layers were combined, dried (Na₂SO₄), and evaporated in vacuo to obtain the desired product (0.5 g., 64.9% from last intermediate), m.p. 137.3°–139.5° C. Recrystallization from benzeneligroin followed by sublimation in vacuo at 130° C. gave an analytical sample, m.p. 156.8°–157.7° C., nmr (CDCl₃): 2.81 (s, 2H, —NH₂); 4.32 (s, 2, —C$\underline{H}$₂—N); 6.29 (d, 1, J=9 Hz, C-3 H); 6.77 (d, 1, J=2.5 Hz, C-4' H); 7.52 (s, 1, C-5 H); 7.75 (poorly resolved m, 2, C-4 H, C-5' H).

Anal. Calcd. for $C_{12}H_9NO_3$: C, 66.97; H, 4.22; N, 6.51. Found: C, 66.74; H, 4.27; N, 6.40.

8-AMINOETHYLPSORALEN

In the same manner as given in the foregoing, but starting from 8-ethylpsoralen in Preparation 2, or from 7-allyloxy-8-ethylcoumarin in Preparation 1, the title compound is produced.

In the same manner as given in the foregoing, other variations in selection of starting materials are productive of still other 8-aminoloweralkylpsoralens, within the scope of the invention, in which the loweralkyl group is varied. As used herein, the term "loweralkyl" comprehends such straight or branched radicals or groups having one to eight carbon atoms, preferably one to four carbon atoms, inclusive, such as methyl, ethyl, propyl, isopropyl, butyl, and the like.

When isolating compounds of the invention in the form of an acid addition salt, the acid is preferably selected so as to contain an anion which is non-toxic and pharmacologically acceptable, at least in usual therapeutic doses. Representative salts which are included in this preferred group are the hydrochlorides, hydrobromides, sulphates, acetates, phosphates, nitrates, methanesulphonates, ethanesulphonates, lactates, citrates, tartrates or bitartrates, and maleates. Other acids are likewise suitable and may be employed if desired. For example, fumaric, benzoic, ascorbic, succinic, salicylic, bismethylenesalicylic, propionic, gluconic, malic, malonic, mandelic, cinnamic, citraconic, stearic, palmitic, itaconic, glycolic, benzenesulphonic, and sulphamic acids may also be employed as acid addition salt-forming acids.

PHARMACOLOGY

The biophotosensitization activity of the compounds of the invention is minimal in the erythemal response test according to the procedure of Pathak and Fitzpatrick, J. Invest. Dermatol. 32, 509–518 (1959), entitled "Bioassay of Natural and Synthetic Furocoumarins (Psoralens)", and usually employed standard modifications thereof. As "biophotosensitization activity" is employed herein, however, as well as "photochemical sensitivity on the skin of a mammal", and "photosensitizing" or "photosensitization", as well as "photochemotherapy", the compounds of the invention are active biophotosensitizing agents inasmuch as they produce solely or at best a preponderance of monoaddition or monofunctional addition in the standard tests for DNA photoreactivity, said monofunctional addition being opposed to interstrand cross-linking, as explained in the foregoing. The compounds are thus clearly useful in the further study of reactions and secondary structures of nucleic acids and as inhibitors of RNA replication, and are indicated for employment in the inactivation of viruses as well as in the photochemotherapy of psoriasis and/or tanning by the PUVA procedure, in which they are found to be equally as effective as numerous previously-employed psoralen compounds, without the production of excessive erythema, if any, which is of course dependent upon numerous factors, such as amount of irradiation employed, dosage of the photosensitizing agent, mode of employment (whether topical or oral), and individual skin sensitivities of the mammal subjected to the PUVA therapy, including of course human beings, with respect to which psoriasis is a unique malady. The compounds are accordingly useful for all of the foregoing purposes, but particularly for effecting photochemical sensitivity on the skin of a mammal, these terms as employed herein not being restricted to the production of erythema thereon. They are effective both orally and topically, and the method of effecting photochemical-sensitivity on the skin of a mammal merely comprises the step of orally or topically administering to the said mammal an effective photosensitizing dose of a compound of the invention. When the subject is then exposed to ultraviolet radiation, more particularly ultraviolet "A", in the non-burning range, monofunctional adducts are formed, tanning occurs, and psoriasis is mitigated in human patients, as aforesaid. Other uses of the compounds of the present invention are also set forth in the foregoing.

ERYTHEMA

The erythematic activity of the compounds of the present invention was determined by visual grading of erythemal response according to a modification of the procedure of Pathak and Fitzpatrick, J. Invest. Dermatol. 32, 509–518 (1959), entitled "Bioassay of Natural and Synthetic Furocoumarins (Psoralens)". (The psoralens are of course "linear" isomers of the furocoumarin family.) According to this bioassay, erythema production on albino guinea pig skin is measured visually and the response accorded a gradation definition according to a 0, ∓, 1, 2, 3, and 4 scale. The modification employed involved variation of the time between administration of the test compound and exposure to ultraviolet light, thereby enabling measurement of times of onset and decline of the induced erythematic photosensitivity effect.

PROTOCOLS—ERYTHEMA

Each drug is tested orally by administering a dosage of forty (40) mgm/kgm of body weight to groups of fifteen female Hartley albino guinea pigs. The appropriate dosage for each animal is packed into a gelatin capsule and placed far back in the animal's pharynx. Swallowing is assisted by syringe delivery of one to three milliliters of water. The animals are not allowed to eat or drink six hours before and after administration of each product. The exposure to ultraviolet "A" radiation is for two (2) minutes at a dose of 1.14 joules per square centimeter at different times after administration, e.g., 10, 20, 30, 45, 60, 90, 120, 180, 240 minutes after administration. Readings and evaluations are carried out 48 hours post ingestion. Irradiations were made on depilated regions of the mid-dorsal area of the back in discrete areas (0.5 cm$^2$) using adhesive tape templates. The rest of the animal was covered in black paper.

Gradation: Responses are graded as follows:
0 No response, ± faint erythema; 1+ erythema; 2+ erythema and slight edema; 3+ erythema and intense edema; and 4+ vesiculobullous reaction.

RESULTS—ERYTHEMA

The compounds of the invention show no oral erythematic activity as read at 48 hours. The compound 8-aminomethylpsoralen (E-122), made from 8-methylpsoralen as in the foregoing, shows no photosensitizing response orally at any post-ingestion time (except a single 1+ response at ninety minutes), as read at 48 hours after ingestion for UVA applications at ten (10) through 240 minutes after ingestion, and a low order of oral toxicity, no animals dying at the dosage level tested. In contrast, the control methoxsalen (8-methoxypsoralen), at the same dose level, exhibits a 48-hour after ingestion erythema reading as follows, with the UVA application being at 10, 20, 30, 45, 60, 90, 120, 180 and 240 minutes after ingestion: 0, 0, 1+, 3+, 3+, 3+, 4+, 3+, 2+. The compound E-122 is therefore essentially inactive erythemically.

However, in the standard DNA-binding test (references given herein under "Prior Art"), identical amounts of the compound E-122 and 8-methoxypsoralen (8-MOP) exhibited the following DNA-binding activity:

E-122 1.4±0.6
8-MOP: 1 (arbitrarily assigned as standard)

PROTOCOLS—DNA-BINDING TEST

Results—Erythema vs. DNA-monoaddition

According to this DNA unwinding test, stock solutions of the test compounds are prepared and dissolved in absolute ethanol. These stock solutions are used to determine specific absorption coefficients in terms of absorption per microgram of the test compound. Ethanol volumes are kept as low as possible to eliminate the possibility of alteration of the DNA structure. Concentrations of the concentrated, sometimes "saturated", stock solutions are determined by dilution into water and using the specific absorption coefficients determined on the standardized solutions prepared as first-above set forth. All of the absorption spectra are taken in de-ionized water with an ethanol concentration of four percent (4%) or less.

Each sample is then irradiated at a minimum of four (4) ratios of drug to DNA with two (2) irradiation times at each ratio. The irradiation intensity is 1.5 mW/cm$^2$ using black light bulbs (F 20 T 12 BLB-GE). Weight ratios of test compound to DNA are varied over three (3) orders of magnitude for each test compound, and the irradiation times are two (2) hours and twenty (20) hours. Irradiations are performed at 4° C.

Agarose gel electrophoresis is employed to analytically separate linear DNA molecules on a basis of molecular weight, lower molecular weight fragments migrating faster on the gel. Agarose can, under appropriate conditions, also resolve molecules of identical molecular weight, but having different conformations. In fact, supercoiled (Form I), nicked-circular (Form II), and linear (Form III) DNA molecules can be resolved, and this capacity for separation or resolving molecules of identical molecular weight but with different conformations is the basis for the psoralen unwinding assay.

The starting DNA sample consists of a mixture of supercoiled (Form I) (fast-running major band) and nicked-circular (Form II) (slower-running, less intense band). Under the conditions employed, full-length linear DNA migrates between supercoiled and nicked-circular DNA. The less intense, slowest-moving bands, are simply dimer and trimer length molecules which repeat the monomer distribution.

Upon photo-reaction with typical psoralen derivatives, according to the foregoing protocol, the DNA helix unwinds proportionately to the extent of photo-reaction. The unwinding of the DNA helix reduces the super-helical density of the DNA, causing the DNA to migrate more slowly on the agarose gel. Thus, any photo-reaction which causes DNA unwinding, DNA nicking, or DNA fragmentation, can be readily detected with the foregoing agarose gel assay.

In the foregoing psoralen DNA unwinding test procedure, the figure 1.4±0.6 determined for the compound E-122 is definitely indicative of monoaddition or monofunctional DNA-binding activity, as opposed to cross-linking activity. In contrast thereto, for example, highly erythemic compounds which cause extremely strong erythemic reactions upon exposure to identical irradiation conditions show a DNA-binding activity in this test as great as 8±4, which is clearly indicative of cross-linking, a conclusion which is also supported by their highly erythemic activity in the usual erythema test, which is fully discussed in the foregoing.

Therefore, according to the DNA-binding test, the compound E-122 exhibits a somewhat greater order of effectiveness than does the compound 8-methoxypsoralen, a commonly-employed and widely-recognized photosensitizing agent, without however exhibiting the erythema which is concurrent upon the employment thereof.

COMPOSITIONS AND METHOD OF TREATING

The pharmaceutical compositions according to the present invention are suitable for use in effecting photochemical sensitivity on the skin of a mammal, particularly a human patient or subject, and comprise an effective amount of a compound of the invention in association with a pharmaceutically-acceptable carrier or diluent. Such compositions are well-known in the art, and reference may again be made to U.S. Pat. Nos. 4,124,598 and 4,130,568 for representative examples and disclosure concerning the same. The procedure for preparation of such compositions is conventional in the art. For tanning or oral treatment of psoriasis, the active ingredient is generally formulated in tablets or in gelatin capsules. In such case the diluent may, if desired, be eliminated, although it is generally present. For topical application, solutions or ointments may be prepared and employed. These may be formulated with any one of a number of pharmaceutically-acceptable carriers, as is well known in the art. Administration may be, for example, in the form of tablets, capsules, powders, syrups, or solutions, or as already stated in the form of ointments, creams, or solutions for topical use. For tablet preparation, the usual tablet adjuvants such as cornstarch, potato starch, talcum, magnesium stearate, gelatin, lactose, gums, or the like may be employed, but any other pharmaceutical tableting adjuvants may also be used, provided only that they are compatible with the active ingredient. In general, an oral dosage regimen will include about 10 mg. to about 50 mg. per kg. of body weight, with a dose in the neighborhood of about 20 mg. per kg. generally being preferred. Such administration and selection of dosage and unit dosage will of course have to be determined according to established medical principles and under the supervision of the physician in charge of the PUVA therapy involved. For topical use, only an effective amount of the active ingredient per unit area is involved, and this will illustratively be in the form of a one percent solution, suspension, or ointment thereof, illustratively applied on the order of one-tenth milliliter per square centimeter, in association with a suitable carrier, e.g., ethanol, or other carriers of the type already mentioned.

It is to be understood that the invention is not to be limited to the exact details of operation or exact compounds, compositions, methods, or procedures shown and described, as obvious modifications and equivalents will be apparent to one skilled in the art.

I claim:
1. 8-primaryaminoloweralkylpsoralen.
2. A compound of claim 1 which is 8-aminomethylpsoralen.
3. The method of effecting photochemical sensitivity on the skin of a mammal comprising the step of orally administering to the said mammal an effective photosensitizing dose of a compound of claim 1.
4. The method of claim 3 wherein the compound is 8-aminomethylpsoralen.
5. A pharmaceutical composition suitable for use in effecting photochemical sensitivity on the skin of a mammal comprising an effective amount of a compound of claim 1 and a pharmaceutically-acceptable carrier of diluent.
6. The composition of claim 5 wherein the compound is 8-aminomethylpsoralen.

* * * * *